United States Patent [19]

Muszak

[11] Patent Number: 5,109,728
[45] Date of Patent: May 5, 1992

[54] LOCKING MEANS FOR A ROTATIONAL WORK STATION IN AN ANALYZER

[75] Inventor: Martin F. Muszak, Rochester, N.Y.
[73] Assignee: Eastman Kodak Company, Rochester, N.Y.
[21] Appl. No.: 736,277
[22] Filed: Jul. 25, 1991
[51] Int. Cl.5 ............................................. F16H 25/00
[52] U.S. Cl. ..................................... 74/820; 74/435; 74/530
[58] Field of Search ..................... 74/74, 99 A, 337.5, 74/435, 437, 530, 568 T, 820

[56] References Cited

U.S. PATENT DOCUMENTS

2,881,630 4/1959 Opocensky ............................ 74/435
3,101,586 8/1963 Polonsky et al. .................... 368/263

Primary Examiner—Leslie A. Braun
Assistant Examiner—William O. Trousdell
Attorney, Agent, or Firm—Dana M. Schmidt

[57] ABSTRACT

There is disclosed a camming apparatus for a work station that provides for relative rotational motion between a cam and a cam follower connected to the work station, e.g., a liquid dispenser. The cam follower is movable on a carrier that frictionally engages the cam, unless the carrier is restricted. The cam is rotated by a gear. A locking mechanism is provided to lock the carrier against inadvertent rotation, and the improvement resides in the locking mechanism comprising a gear segment on the cam follower positioned to engage the gear during a portion of the engagement by the drive gear of the gear segment on the cam.

7 Claims, 9 Drawing Sheets

FIG. 10 (COMPARATIVE EXAMPLE)

LOCKING MEANS FOR A ROTATIONAL WORK STATION IN AN ANALYZER

FIELD OF THE INVENTION

The invention relates to apparatus for easily locking a movable work station from inadvertent movement, particularly work stations involving a camming mechanism.

BACKGROUND OF THE INVENTION

In commonly owned U.S. Pat. Ser. No. 726,138, which is a continuation of U.S. Pat. Ser. No. 556,692, filed on Jul. 20, 1990 by Shaw et al, entitled "Dispenser Mechanism", there is disclosed a work station comprising a dispensing pump mechanism that automatically raises and rotates a dispenser from one position to another. This is particularly useful in a blood analyzer. The mechanism features a dispenser and a cam follower mounted for vertical movement on an outer carrier. The carrier frictionally engages a cam track that is formed on a cam that fits inside the carrier and is rotated by a pinion gear. As long as the carrier and the cam rotate together, the pump dispenser rotates without changing elevation. However, when the outside carrier hits one of two mechanical stops, it ceases to rotate while the cam continues to rotate, forcing the cam follower and dispenser to move along the cam track. The change in vertical height along the cam track produces the vertical motion of the dispenser.

This mechanism has been found to work quite well. However, to arbitrarily hold the carrier against rotation, such as when maintenance is needed, a ring of teeth is used on the carrier, to be engaged with a solenoid—activated lever. The solenoid is an additional mechanism that adds cost and maintenance to the mechanism. Therefore, prior to this invention, there has been a need to improve the mechanism by eliminating the need for the solenoid and its lever, while retaining the function of being able to lock the carrier against inadvertent rotation.

SUMMARY OF THE INVENTION

I have solved the above problem by utilizing a part of the mechanism already in place, namely the pinion gear that rotates the cam inside the carrier.

More specifically, in accord with one aspect of the invention there is provided a camming apparatus for raising and lowering a work station in response to a rotational drive, the apparatus comprising a cam, means for mounting the cam for rotation, drive means for rotating the cam and including a drive gear and a gear segment on the cam, a carrier for mounting a cam follower on said cam, said carrier being frictionally mounted on the cam sufficient to cause the follower to rotate with the cam, unless the carrier is held from rotation, and locking means to lock the carrier into a known position to permit adjustments. The apparatus is improved in that the locking means comprise a gear segment on the carrier positioned to engage the drive gear during a portion of the engagement by the drive gear of the gear segment on the cam.

When driving two relatively independent gear segments by a single pinion gear, one of which is engaged only part of the time, it is not sufficient that the one which is engaged only part-time be constructed with normal gear teeth. The reason is that as the part-time segment comes to the pinion gear, it is possible for the teeth on the gear segment to mismatch with the teeth on the pinion gear, thus locking up or breaking the gearing.

Thus, in accord with another aspect of the invention, this subsidiary problem is solved by providing a gear drive comprising a drive gear and a segment of a driven ring gear that rotates into and out of engagement with the drive gear along a pitch circle, the ring gear segment having opposite ends with gear teeth extending at uniformly spaced intervals between the ends. The gear drive is improved in that the gear segment further includes at the opposite ends means for smoothly engaging the pinion gear as the segment moves into the path of the drive gear, the means comprising the sizing of the very first gear tooth in the segment at each of the ends so that its height is less than the distance of projection of the pitch circle.

Accordingly, it is an advantageous feature of the invention that a work station which normally is free to rotate relative to a driving cam, is lockable against such rotation by using the same drive gear that is used to drive the drive cam.

It is a related advantageous feature that the locking provided as noted features a gear segment on the rotating work station that is constructed to repeatedly smoothly engage the drive gear, without jamming.

Other advantageous features will become apparent upon reference to the following Detailed Description when read in light of the attached drawings.

DESCRIPTION OF THE PREFERRED EMBODIMENTS

The invention is hereinafter described by reference to the preferred embodiments, in which a work station to be manipulated is a dispenser of a reference liquid used for potentiometric measurements or for a wash, as shown with an analyzer of a particular construction. In addition, the invention is also useful to manipulate any work station, regardless of the end use of that work station.

ENVIRONMENT OF PREFERRED USE

Figure 1:
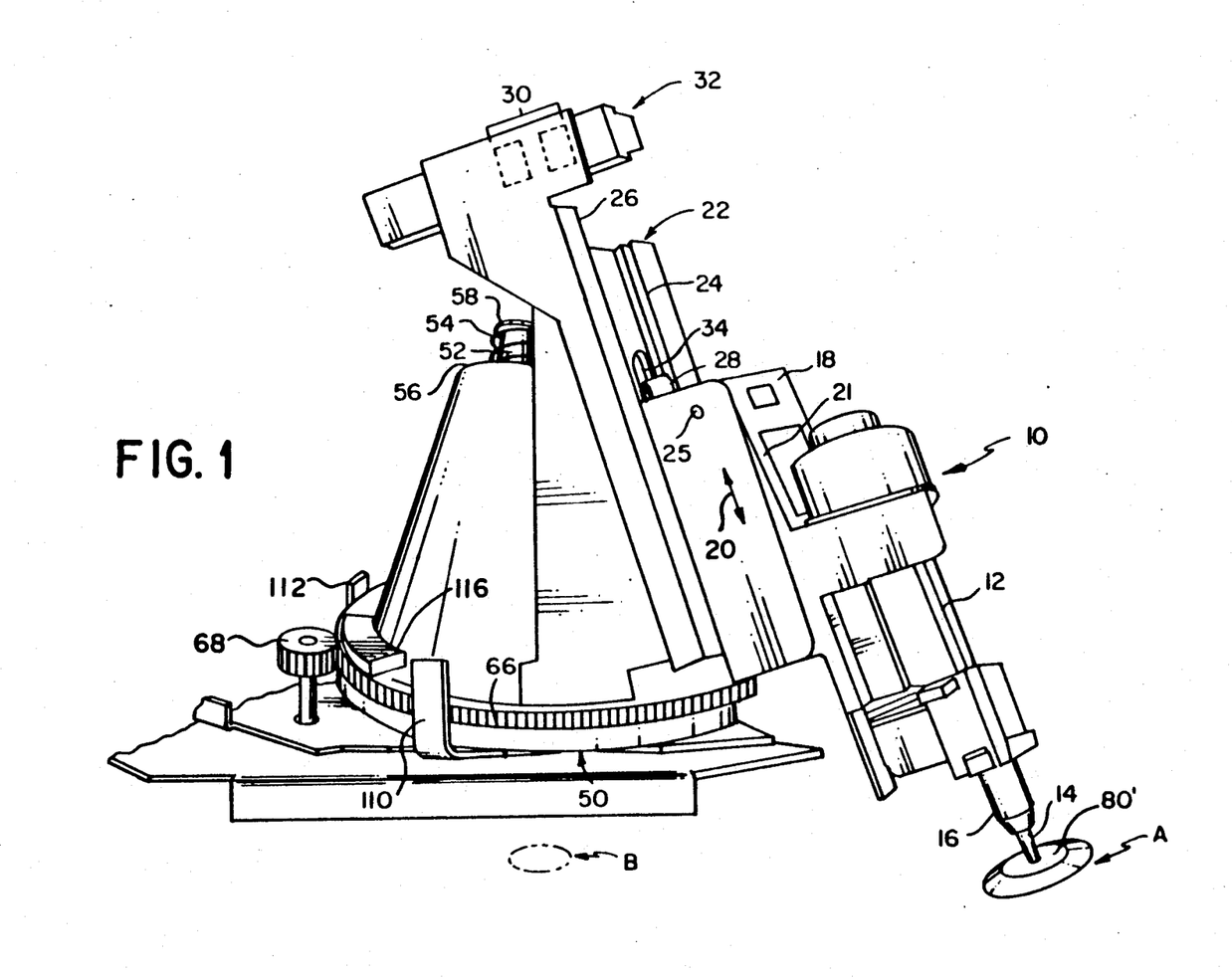
FIG. 1 is a perspective view of a liquid-aspirating and dispensing mechanism with which the invention is useful.
Figure 2:
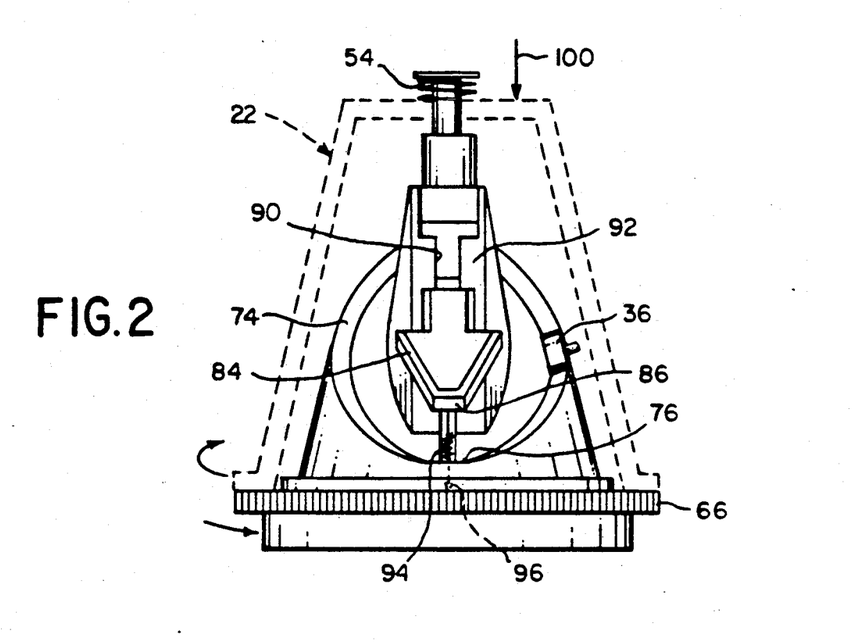
FIG. 2 is a fragmentary elevational view of the cam of the assembled mechanism of FIG. 1, showing the cam follower at a raised position at which the pump dispenser is inoperative, and the pump carrier in phantom.
Figure 7:
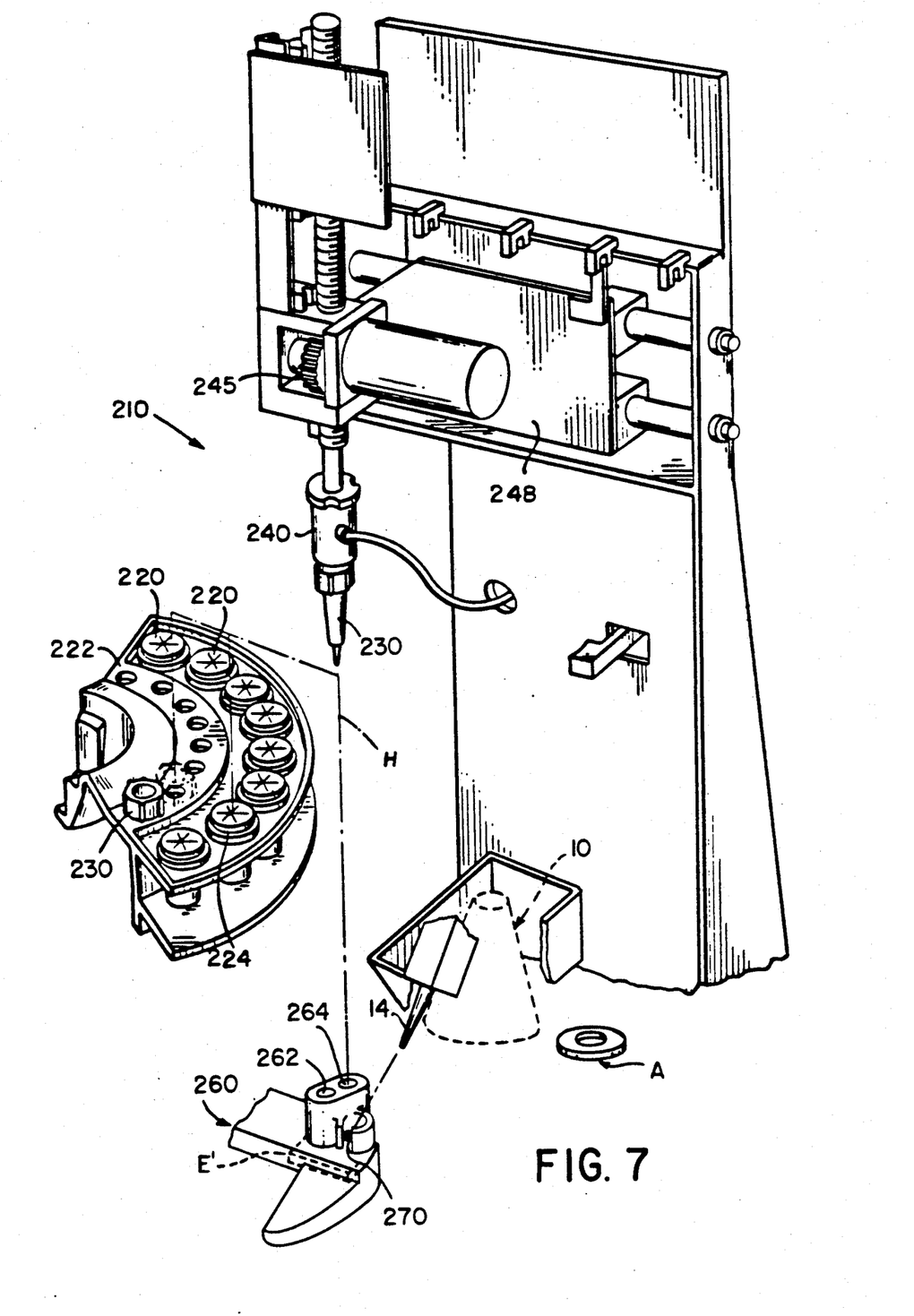
FIG. 7 is a perspective view illustrating the positioning of the mechanism of FIG. 1 in a clinical analyzer.

As disclosed and claimed in the aforesaid U.S. Pat. Ser. No. 726,138 which is a continuation of U.S. Pat. Ser. No. 556,692 liquid dispensing mechanism useful with the invention is shown in FIG. 1, to allow aspiration of liquid from station A, a reservoir of the liquid, and the dispensing of a fraction or aliquot of the liquid so aspirated, at station B. These same stations are also shown in FIG. 7, described hereinafter. Alternatively, the positions of stations A & B can be reversed in some uses.

More specifically, the liquid dispensing mechanism 10 comprises a pump 12 of conventional construction similar to that used in the analyzer pump available on the analyzer from Eastman Kodak Company under the trademark "Ektachem 700", carrying a disposable tip 14 on a tip support 16. Pump 12 includes a housing 18 to which pump 12 is connected. Preferably, housing 18 of pump 12 comprises, FIG. 4, a body 19 that has a yoke 21 extending therefrom to two lugs 23 that pivot to frame 18 at 25. Housing 18 reciprocates, arrow 20, FIG. 1, on a carrier 22 having opposite rails 24, 26 between which housing 18 slides. A position-sensor flag 28 is mounted on the top of housing 18 to cooperate with sensing means 30 located at the top 32 of carrier 22. See also FIG. 3.

Carrier 22, FIG. 1, is shaped to slip over a cam mechanism 50 that carrier 22 frictionally engages. A slot 34 is formed in carrier 22 between rails 24, 26 to allow a cam follower 36, FIG. 4, and its idler arm 38, to project through. Arm 38 is fixed to pump 12 or its housing 18. Preferably, a shoulder 40 projects pump 12 or its housing to also guide the pump within slot 34.

Figure 4:
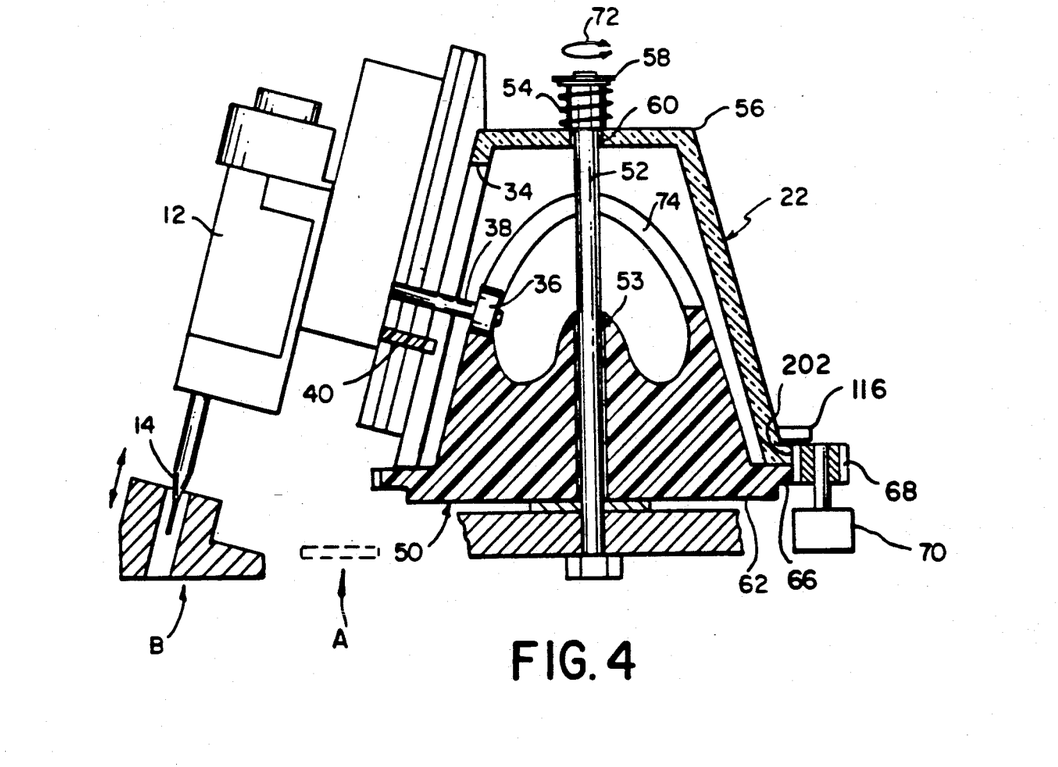
FIG. 4 is an elevational view in section, showing the locking of the carrier by the invention.

The frictional engagement of cam 50 by carrier 22 is preferably achieved. FIGS. 1 and 4, by a central fixed post 52 that passes through center portion 53 of the cam, FIG. 4, a compression spring 54 surrounding the post and bearing on end wall 56 of carrier 22, and a retaining clip 58. End wall 56 is apertured at 60, FIG. 4, to accommodate post 52 that projects therethrough.

Bottom wall 62 of cam 50 adjoins a curved sidewall 64 that is preferably provided with gear teeth 66. Most preferably, sidewall 64 at the teeth portion 66 is circular. Gear teeth 66 are positioned and shaped to engage a pinion gear 68 driven by a conventional motor 70, to cause cam 50 to rotate about the axis of post 52, arrow 72.

Figure 3:
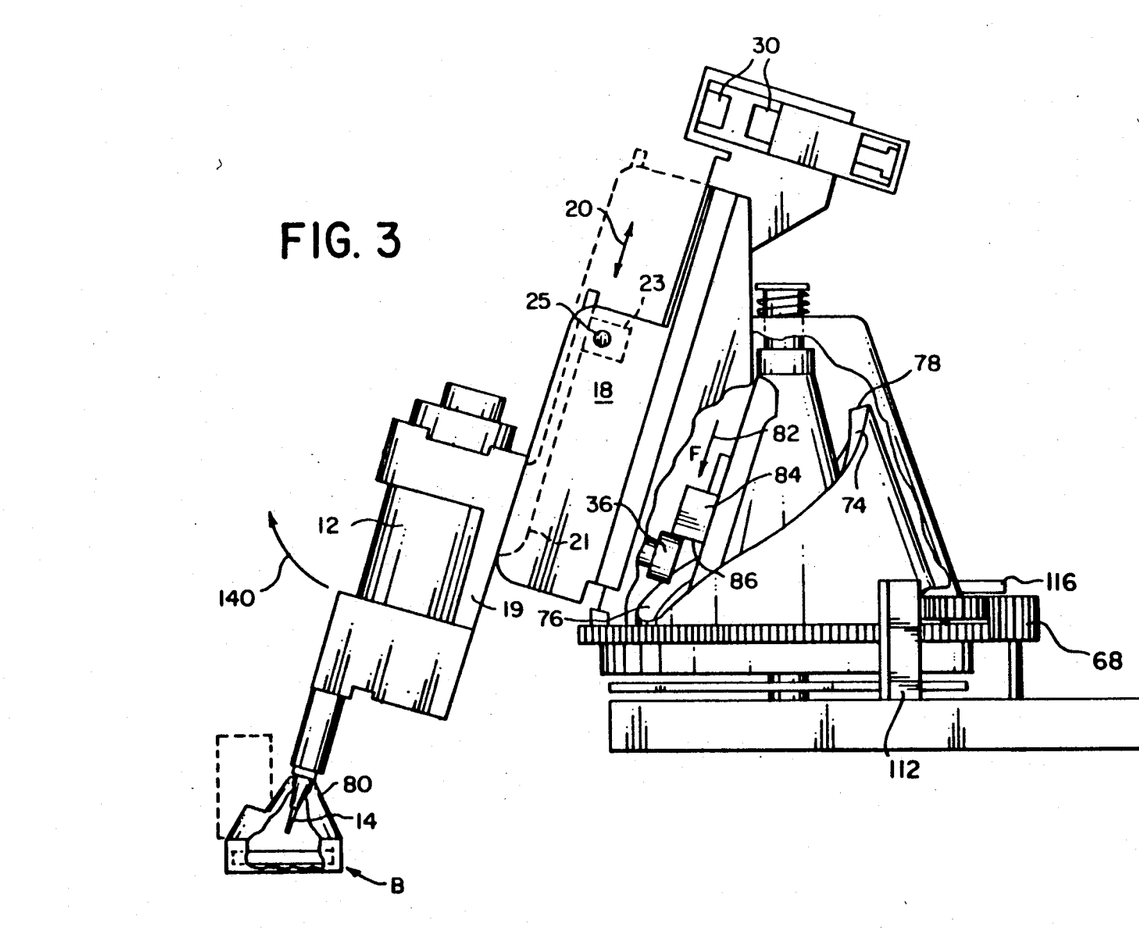
FIG. 3 is a partially broken away, elevational view but illustrating the cam follower in its lowermost position, wherein it is biased by the down-loading cam.

A critical aspect of cam 50 is cam track 74, extending in three dimensions around post 52, as shown in FIGS. 2, 3, 4, and 5A-5B. Track 74 includes a bottom-most portion 76, FIGS. 3 and 5B, and all the rest of the track that rises above that portion to completely encircle post 52, FIG. 4. Because cam 50 is preferably conical in overall shape as shown in this embodiment, track 74 also traces the surface of the cone defined by this portion of cam 50. The uppermost portion 78 of track 74 is generally opposite to the lowermost portion 76, that is, on the opposite side of post 52, as best shown in FIG. 3.

Cam follower 36 rides on track 74 due to gravity, except when pump carrier 22 and its cam follower are at bottom portion 76. At this time, the pump is at one of the two operative stations A or B, station B being schematically shown in FIG. 1 and partially schematically in FIG. 3. At either station, a top surface 80 or 80' is effective to resist further downward advance of tip 14 or pump 12. As a result, cam follower 36 is lifted off of track 74. However, to be sure that tip 14 is in fact completely seated at the station (for dispensing or aspirating, as the case may be), means are provided for biasing the cam follower downward with a predetermined positive force F, arrow 82, FIG. 3. Such means preferably comprise a downwardly-directed camming surface 84, preferably V-shaped with the bottom-most portion 86 representing the complete sealing position of cam follower 36, and hence of tip 14 at either station A or B. See especially FIG. 2.

To bias camming surface 84 downwardly, that surface is slidably mounted in a track 90 on face 92 of cam 50. Inside track 90, a tension spring 94 is connected at one end to surface 84, and at its opposite end 96 to cam 50.

Because of the downward force F, arrow 100 (FIG. 2), exerted by spring 54, pump carrier 22 generally rotates with cam 50 as it is driven to rotate. However, means are provided, such as two limit members 110 and 112 fixed to support 114 of mechanism 10, FIG. 1, to stop rotation of carrier 22 and to confine its rotation within the arc between members 110 and 112. An outwardly projecting lip 116 is formed integral with carrier 22, FIG. 1 and especially FIGS. 5A and 5B. Lip 116 is sized and positioned to abut against either limit member 110 or 112 as cam 50 rotates, arrow 118, FIGS. 5A and 5B. The effect, of course, is to cause carrier 22 to come to a stop at a limit member, e.g., member 110, FIG. 5B, while cam 50 continues to rotate inside carrier 22. That is, gear tooth X, FIG. 5A, continues to rotate to its position shown in FIG. 5B, even though carrier 22 does not progress beyond the position shown in FIG. 5B. This in turn causes cam track 74 (in phantom) to continue to rotate relative to the now stationary carrier 22, as is shown by the relative positional changes of track 74 in FIG. 5B from that of FIG. 5A. Cam follower 36 in turn is forced, along with the pump and tip 14, to rise up since track 74 is "rising", arrow 120, FIG. 5B. In the raised "inoperative" position shown in FIG. 5B (in phantom), the pump and tip 14 are in position to be rotated (arrow 122) from that station (station A) to station B, without bumping into structure that is otherwise in the way. This is achieved by reversing the rotation of cam 50, arrow 124, at which time carrier 22 again moves with cam 50 until the other limit member (112, not shown in FIG. 5B) encounters lip 116 to force carrier 22 to once again stop while cam 50 continues in the direction of arrow 124.

THE LOCKING MEANS

Because the same reference liquid is aspirated from station A for many tests, tip 14 need not be replaced frequently. However, it is replaced for maintenance and cleanliness on occasion, e.g., every day, and for this purpose, means are included for removably locking carrier 22 to its last known position while tip 14 is manually removed. It is in this locking means that the present invention resides.

Figure 5A:
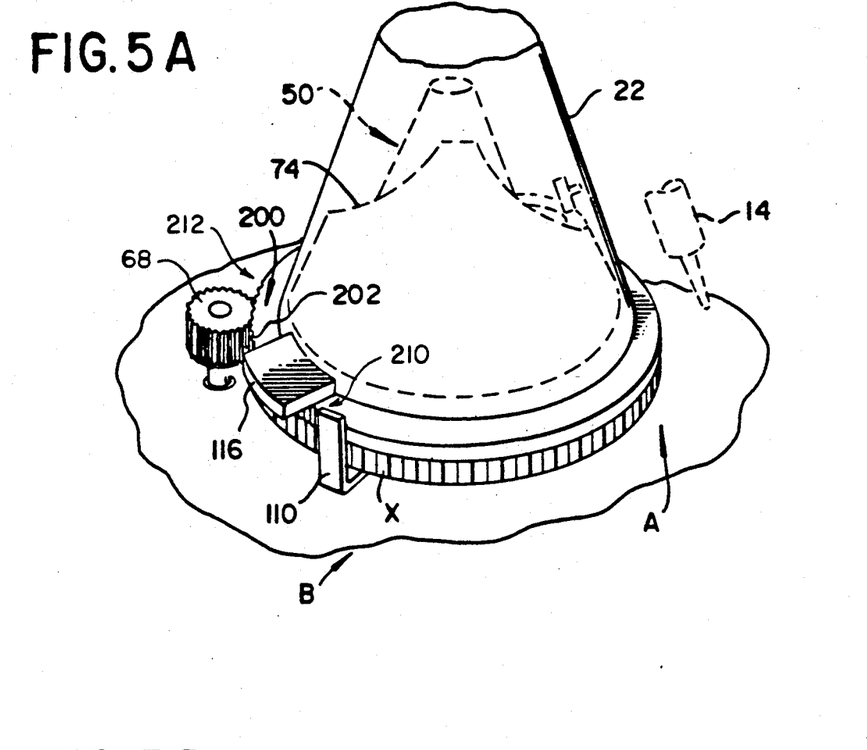
FIG. 5A and 5B are fragmentary perspective views of the pump carrier and the cam (shown in phantom) to illustrate the relative movement between the two.
Figure 8:
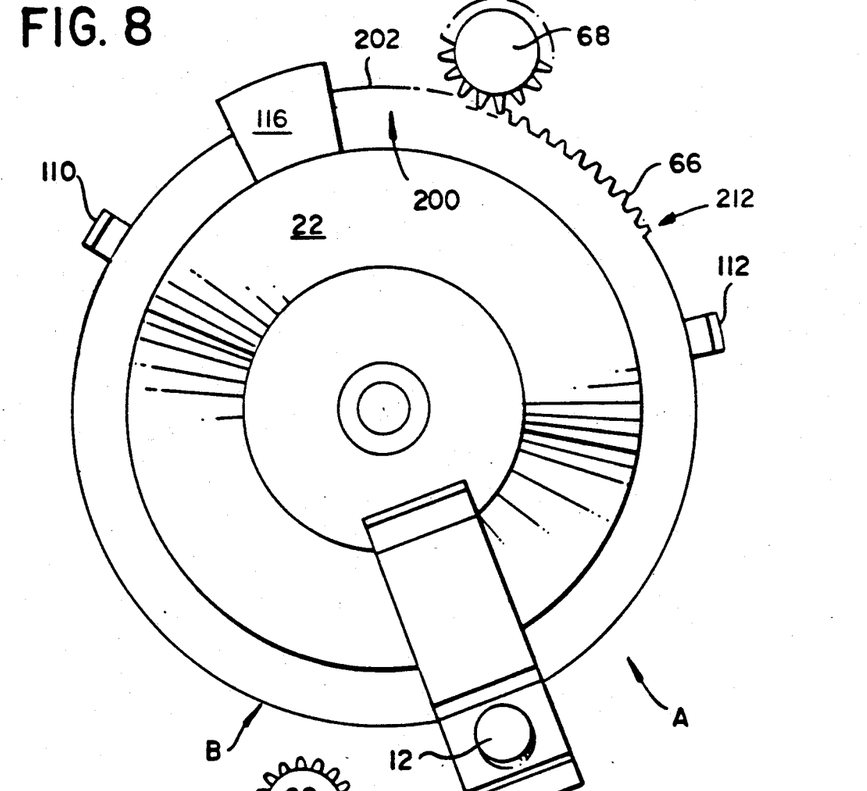
FIG. 8 is a fragmentary plan view of the mechanism of FIG. 1, further illustrating the invention.

That is, in accordance with one aspect of the invention, the pinion gear 68 used to drive cam 50 is also used to "lock up" carrier 22 by means of a ring gear segment 200, FIGS. 5A and 8 extending from carrier 22 immediately adjacent to gear teeth 66 of cam 50. Segment 200 has gear teeth 202, FIGS. 4, 5A, 5B, and 9, appropriately shaped to also engage pinion gear 68. That is, except at the ends 210 and 212 of segment 200, teeth 202 are identical in shape and size as teeth 66, so as to mate with gear 68. As a result, when carrier 22 is in the position shown in FIG. 8, gear 68 is locked with carrier 22 and cam 50, so that maintenance can be performed on pump 12 without rotationally disturbing carrier 22 on cam 50. In fact, with motor 70 turned off, the resistance of gear 68 is such as to make any manual rotational movement of carrier 22 and cam 50 unlikely.

Figure 5B:
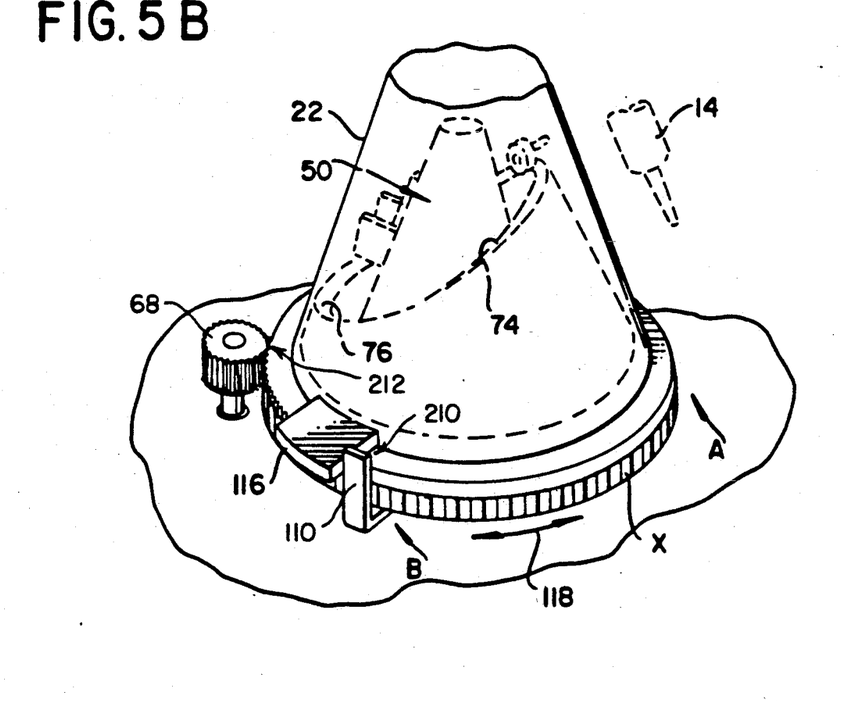
Figure 6:
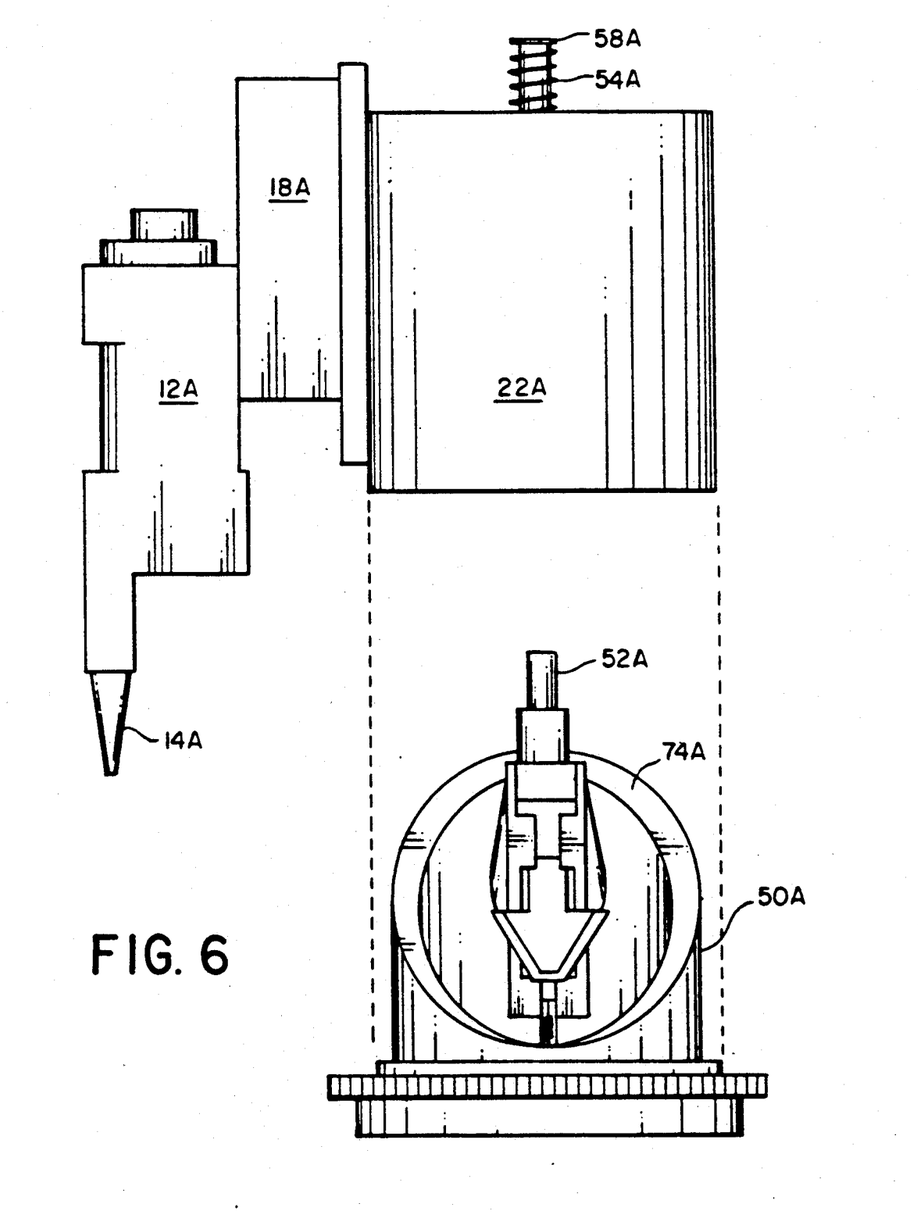
FIG. 6 is an exploded elevational view similar to that of FIG. 1, but illustrating an alternate embodiment of the invention.
Figure 6A:
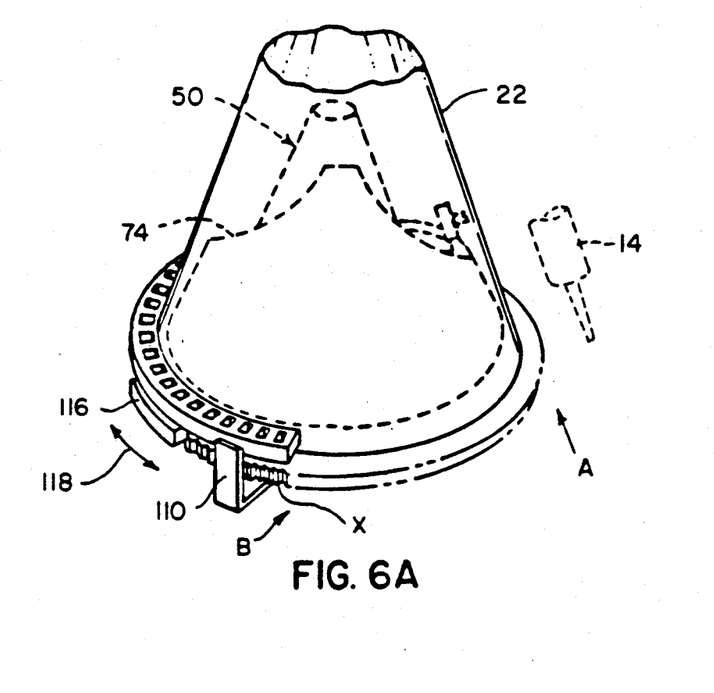
Figure 6B:
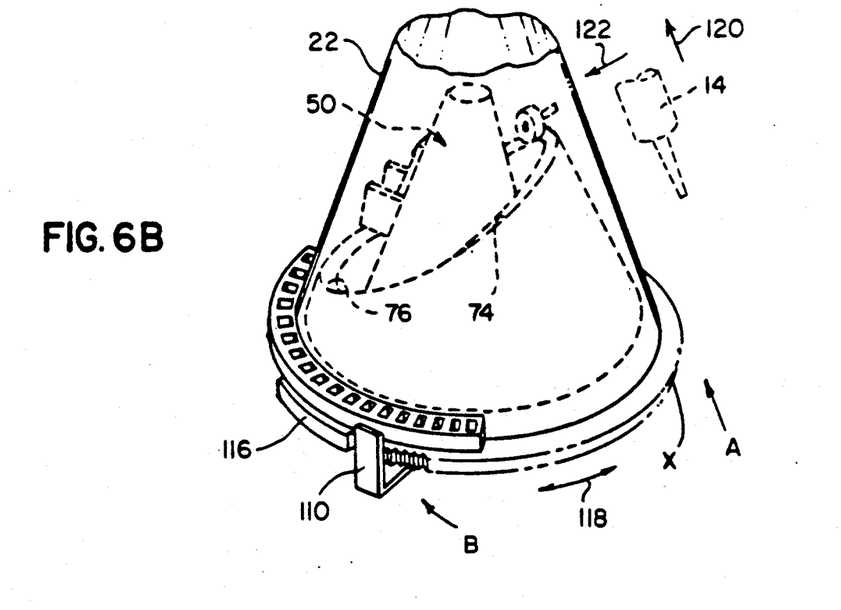

Ends 210 and 212 are carefully located, as shown particularly in FIGS. 5A & 5B, so that gear 68 is free of engagement with teeth 202 when lip 116 has contacted either limit member (member 110 in FIG. 5B). (Limit member 112 cannot be seen in FIG. 5A as it is behind carrier 22.) By such means, gear 68 can continue to rotate cam 50 without rotating carrier 22.

As noted above, it is preferred that the ends 210 and 212 of segment 200 be specially constructed to be different from teeth 202 in between those ends.

Figure 9:
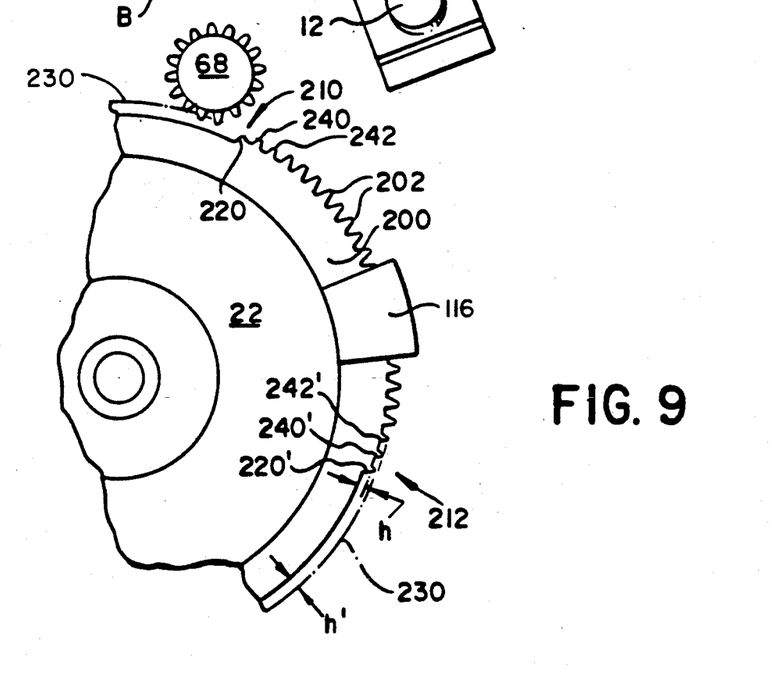
FIG. 9 is a fragmentary schematic view, in plan, of the engagement of the drive or pinion gear with the gear segment of the carrier of the work station.

More specifically, FIG. 9, the preferred construction of ends 210 and 212 is that first gear tooth 220 and 220' (first when viewed from either end) has a height "h" that is less than the projection h' of the pitch circle 230 for gear segment 200 and gear 68. As used herein, "pitch circle" means the circle formed by the pitch diameter in mm which in turn, in the metric system equals the module of the gear times the number of teeth.

This reduced height tooth is particularly effective in slipping tooth 220 or 220', and thus all remaining teeth 202, into engagement with gear 68 without jamming. In fact, I have found that a tooth smaller than teeth 202, but having a height that projects out beyond pitch circle 230, for example as with tooth 68, FIG. 4 of U.S. Pat. No. 3,101,586, tends to cause jamming of segment 200 with gear 68. The reason is that, unlike the construction in the '586 patent, there is insufficient compliance in the horizontal plane to accommodate the jamming condition shown in FIG. 4 of the '586 patent. (Sufficient compliance in the horizontal plane is not tolerable at the instant work station since that will tend to improperly locate pump 12 at a different radius than is needed for stations A and B, FIG. 8. Rather, the compliance in this device is an axial and pivotal compliance created by spring 54 being mounted at the top, FIG. 4, of axle 52 adjacent washer 58. The top location of the spring allows carrier 22 to move upward if a tooth-to-tooth jam starts to occur. The upward compliance allows realignment of the teeth and horizontal positioning is maintained during metering.

The most preferred construction of ends 210 and 212 proceeds even further, FIG. 9—second and third teeth 240, 242 and 240', 242' are also reduced in height compared to teeth 202. However, these have a height that approximates the distance h' of the projection of pitch circle 230. The purpose is to further ensure smooth engagement of segment 200 by gear 68, such as if and when tooth 220 (or 220') is worn down by usage to prevent automatic engagement.

Figure 10:
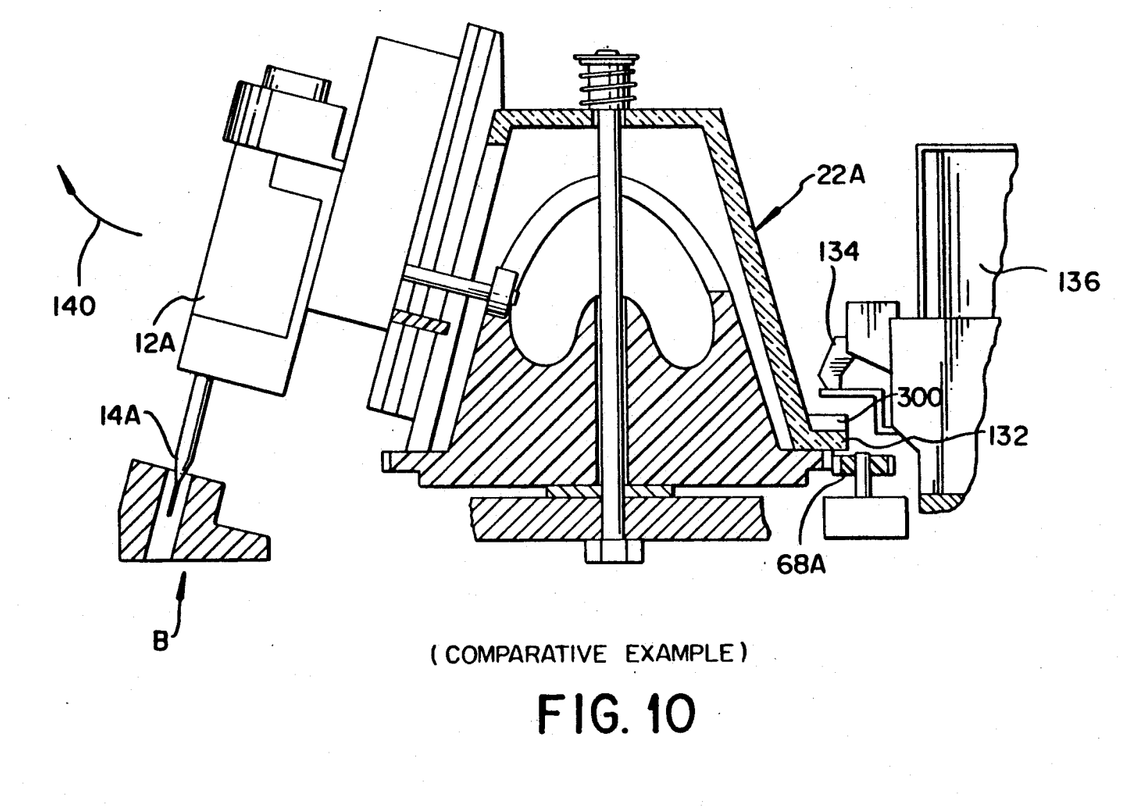
FIG. 10 is a section view similar to that of FIG. 4, but of a comparative example.

As a comparative example, FIG. 10 illustrates the locking means used in the aforesaid application Ser. No. 726,138. Parts previously described have a suffix "A" appended to indicate it is a comparative example. Upwardly projecting teeth 300 are molded into side edge 132 of carrier 22A (these teeth 300 cannot engage gear 68A, which has a shorter height than pinion gear 68 of this invention). Cooperating with teeth 300 is a lock lever 134 actuated by a solenoid 136 to be either in a raised position, as shown, or a lowered position to engage teeth 130 to lock against relative rotation of carrier 22A. Optionally, a tension spring can be used to bias lever 134 upward into its disengaged position, so that solenoid 136 need only lower lever 134. In use, lever 134 is effective to hold carrier 22A in place to allow maintenance of the pump and tip 14A. For such maintenance, the pump 12A is preferably pivoted, arrow 140, upwardly.

By means of the current invention, solenoid 136 and its locking lever 134 are eliminated. No other activating means apart from gear 68 and its motor 70, are present or needed to engage the locking function.

The invention has been described in detail with particular reference to certain preferred embodiments thereof, but it will be understood that variations and modifications can be effected within the spirit and scope of the invention.

What is claimed is:

1. In a camming apparatus for raising and lowering a work station in response to a rotational drive, said apparatus comprising a cam, means for mounting said cam for rotation, drive means for rotating said cam and including a drive gear and a gear segment on said cam, a carrier for mounting a cam follower on said cam, said carrier being frictionally mounted on said cam sufficient to cause said follower to rotate with said cam, unless said carrier is held from rotation, and locking means to lock said carrier into a known position to permit adjustments, the improvement wherein said locking means comprise a gear segment having two ends on said carrier positioned to engage said drive gear during a portion of the engagement by said drive gear of said gear segment on said cam.

2. Apparatus as defined in claim 1 wherein said gear segment on said carrier includes engaging means for smoothly engaging said drive gear as said carrier segment moves into the path of said drive gear.

3. Apparatus as defined in claim 2, wherein said engaging means comprise the sizing of the very first gear tooth in said carrier gear segment at each of said ends so that its height is less than the distance of projection of the pitch circle.

4. Apparatus as defined in claim 3, wherein at least one of the next two of said gear teeth immediately following said very first gear tooth has a height that approximates said distance of projection of said pitch circle.

5. Apparatus as defined in claim 1, wherein said locking means is free of activating means actuated apart from said drive gear.

6. In a gear drive comprising a drive gear and a segment of a driven ring gear that rotates into and out of engagement with said drive gear along a pitch circle, said ring gear segment having opposite ends with gear teeth extending at uniformly spaced intervals between said ends, the improvement wherein said gear segment further includes at said opposite ends means for smoothly engaging said drive gear as said segment moves into the path of said drive gear, said means comprising the sizing of the very first gear tooth in said segment at each of said ends so that its height is less than the distance of projection of said pitch circle.

7. A gear drive as defined in claim 6 wherein at least one of the next two of said gear teeth immediately following said very first gear tooth has a height that approximates said distance of projection of said pitch circle.

* * * * *

UNITED STATES PATENT AND TRADEMARK OFFICE
CERTIFICATE OF CORRECTION

PATENT NO. : 5,109,728
DATED : May 5, 1992
INVENTOR(S) : Martin F. Muszak

It is certified that error appears in the above-indentified patent and that said Letters Patent is hereby corrected as shown below:

In column 3, line 7, insert ", a" after "556,692".

In column 6, line 41 should read "the pitch circle of said carrier gear segment."

Signed and Sealed this

Third Day of August, 1993

Attest:

MICHAEL K. KIRK

*Attesting Officer*   Acting Commissioner of Patents and Trademarks